United States Patent
Von Ramm et al.

(10) Patent No.: US 10,537,309 B2
(45) Date of Patent: Jan. 21, 2020

(54) SYSTEMS AND METHODS FOR ULTRASOUND MOTION DISPLAY AND ANALYSIS

(71) Applicant: DUKE UNIVERSITY, Durham, NC (US)

(72) Inventors: Olaf T. Von Ramm, Efland, NC (US); John C. Moore, Durham, NC (US)

(73) Assignee: Duke University, Durham, NC (US)

(*) Notice: Subject to any disclaimer, the term of this patent is extended or adjusted under 35 U.S.C. 154(b) by 668 days.

(21) Appl. No.: 14/940,216

(22) Filed: Nov. 13, 2015

(65) Prior Publication Data

US 2016/0135790 A1    May 19, 2016

Related U.S. Application Data

(60) Provisional application No. 62/079,024, filed on Nov. 13, 2014.

(51) Int. Cl.
| | |
|---|---|
| *A61B 8/14* | (2006.01) |
| *A61B 8/08* | (2006.01) |
| *G01S 7/52* | (2006.01) |
| *A61B 8/00* | (2006.01) |
| *A61B 8/06* | (2006.01) |

(52) U.S. Cl.
CPC ............ *A61B 8/5207* (2013.01); *A61B 8/145* (2013.01); *A61B 8/4494* (2013.01); *G01S 7/52095* (2013.01); *A61B 8/06* (2013.01); *A61B 8/5223* (2013.01)

(58) Field of Classification Search
CPC ............ G01S 15/8927; G01S 15/8993; G01S 7/5209; G01S 7/52095; A61B 8/06; A61B 8/145; A61B 8/4494; A61B 8/5207; A61B 8/5223; A61B 8/54
See application file for complete search history.

(56) References Cited

U.S. PATENT DOCUMENTS

| | | | |
|---|---|---|---|
| 4,596,145 | A | 6/1986 | Smith et al. |
| 4,694,434 | A | 9/1987 | von Ramm et al. |
| 5,546,807 | A | 8/1996 | Oxaal et al. |
| 6,159,153 | A | 12/2000 | Dubberstein et al. |

(Continued)

OTHER PUBLICATIONS

Name of the author : O. I. von Ramm Title of the article : Cardiac Imaging Using a Phased Array Ultrasound System I. System design Title of the item : Circulation Date : Feb. 1976 pp. 6.

(Continued)

*Primary Examiner* — Mark D Remaly
(74) *Attorney, Agent, or Firm* — NK Patent Law

(57) ABSTRACT

A method of generating an image of a scanned subject includes: emitting, by multiple ultrasonic elements of an array, multiple respective ultrasonic signals into a subject, the multiple respective ultrasonic signals defining at least two beam portions traveling in different directions; receiving, by the multiple ultrasonic elements, multiple respective ultrasonic echo signals; and generating at least one image of a portion of the subject from the received multiple ultrasonic echo signals. A negatively focused wavefront including the at least two beam portions traveling in the different directions may be emitted. Multiple negatively focused wavefronts may be generated and emitted.

15 Claims, 13 Drawing Sheets

(56) References Cited

U.S. PATENT DOCUMENTS

| | | | | |
|---|---|---|---|---|
| 6,527,717 | B1* | 3/2003 | Jackson | A61B 8/485 |
| | | | | 128/916 |
| 2011/0144494 | A1* | 6/2011 | Mehi | B06B 1/0622 |
| | | | | 600/441 |
| 2014/0243614 | A1* | 8/2014 | Rothberg | A61B 8/13 |
| | | | | 600/301 |
| 2015/0265249 | A1* | 9/2015 | Urban | A61B 8/485 |
| | | | | 600/438 |
| 2015/0379736 | A1* | 12/2015 | Thosar | A61B 8/06 |
| | | | | 382/131 |
| 2016/0113624 | A1* | 4/2016 | Katsuyama | A61B 8/0841 |
| | | | | 600/424 |

OTHER PUBLICATIONS

Name of the author : J. Kisslo Title of the article : Cardiac imaging using a phased array ultrasound system. II. Clinical technique and application Title of the item : Circulation Date : Feb. 1976. pp. 7.

Name of the author : P. Kligfield Title of the article : Recommendations for the standardization and interpretation of the electrocardiogram Title of the item : Journal of the American College of Cardiology Date : Mar. 2007.

Name of the author : M. Cikes Title of the article : Ultrafast Cardiac Ultrasound Imaging : Technical Principles, Applications, and Clinical Benefits Title of the item : JACC: Cardiovascular Imaging Date : Aug. 2014 pp. 12.

Name of the author : Michael Tanter Title of the article : Ultrafast Imaging in Biomedical Ultrasound Title of the item : IEEE Transactions on Ultrasonics, Ferroelectrics, and Frequency Control Date : Jan. 2014 pp. 18.

Name of the author : D. P. Shattuck Title of the article : Explososcan: A parallel processing technique for high speed ultrasound imaging with linear phased arrays Title of the item : J Acoust Soc Am. Date : Apr. 1984.

Name of the author : Jensen Title of the article : Field: A program for Simulating ultrasound systems Title of the item : 10th Nordic-Baltic Conference on Biomedical Imaging Date : 1996 pp. 3.

Name of the author : Hideyuki Hasegawa Title of the article : High-frame-rate echocardiography using diverging transmit beams and parallel receive beamforming Title of the item : J Med Ultrasonics Date : 2011.

Name of the author : Raoul Mallart Title of the article : Improved imaging rate through simultaneous transmission of several ultrasound beams Title of the item : SPIE Date : 1992 Pages.

Name of the author : Jensen Title of the article : Calculation of pressure fields from arbitrarily shaped, apodized, and excited ultrasound transducers Title of the item : IEEE Transactions on Ultrasonics. Ferroelectrics. and Frequency Control Date : Mar. 1992.

Name of the author : Arash Kheradvar Title of the article : Echocardiographic Particle Image Velocimetry: A Novel Technique for Quantification of Left Ventricular Blood Vorticity Pattern Title of the item : Journal of the American Society of Echocardiography Date : 2010.

Name of the author : Libertario Demi Title of the article : Implementation of parallel transmit beamforming using orthogonal frequency division multiplexing—Achievable resolution and interbeam interference Title of the item : IEEE Transactions on Ultrasonics Ferroelectrics and Frequency Control Date : Nov. 2013.

Name of the author : Libertario Demi Title of the article : In vitro and in vivo tissue harmonic images obtained with parallel transmit beamforming by means of orthogonal frequency division multiplexing Title of the item : IEEE Transactions on Ultrasonics Ferroelectrics and Frequency Control Date : Jan. 2015.

Name of the author : Hong Title of the article : Characterization and Quantification of Vortex Flow in the Human Left Ventricle by Contrast Echocardiography Using Vector Particle Image Velocimetry Title of the item : JACC Cardiovasc Imaging Date : Nov. 2008.

Name of the author : L. Tong Title of the article : Multi-Transmit Beam Forming for Fast Cardiac Imaging—Experimental Validation and In Vivo Application Title of the item : IEEE Transactions on Medical Imaging Date : Jun. 2014.

Name of the author : E. E. Konotagou Title of the article : Electromechanical wave imaging for noninvasive mapping of the 3D electrical activation sequence in canines and humans in vivo Title of the item : J Biomech. Date : Mar. 15, 2012 pp. 23.

Name of the author : J. Kuo Title of the article : Interactive volume rendering of real-time three-dimensional ultrasound images Title of the item : IEEE Transactions on Ultrasonics, Ferroelectrics, and Frequency Control Date : Feb. 2007 pp. 313-318.

Name of the author : Emmanuel Cherin Title of the article : Ultrahigh frame rate retrospective ultrasound microimaging and blood flow visualization in mice in vivo Title of the item : Ultrasound—in medicine and biology Date : May 2006.

Name of the author : M. Couade Title of the article : Ultrafast imaging of the heart using circular wave synthetic imaging with phased arrays Title of the item : Ultrasonics Symposium (IUS), 2009 IEEE International Date : Sep. 20-23, 2009 pp. 515-518.

Name of the author : Elisa E. Konotagou Title of the article : Noninvasive electromechanical wave imaging and conduction-relevant velocity estimation in vivo Title of the item : Ultrasonics Date : 2010 pp. 8.

Name of the author : J. Provost Title of the article : Mapping of cardiac electrical activation with electromechanical wav imaging: An in silico-in vivo reciprocity study Title of the item : Heart Rhythm Date : May 2011.

Name of the author : Hiroshi Kanai Title of the article : Minute Mechanical-Excitation Wave-Front Propagation in Human Myocardial Tissue Title of the item : Japanese Journal of Applied Physics Date : Jul. 20, 2011 Pages.

Name of the author : Jean Provost Title of the article : A clinical feasibility study of atrial and ventricular electromechanical wave imaging Title of the item : Heart Rhythm Date : 2013 pp. 16.

Name of the author : Birger Brekke Title of the article : Ultra-high frame rate tissue Doppler imaging Title of the item : Ultrasound Med. Biol Date : 2014 pp. 10.

Name of the author : Clement Papadacci Title of the article : High-contrast ultrafast imaging of the heart Title of the item : IEEE Trans. Ultrason. Ferroelectr. Freq. Control Date : Feb. 2014 pp. 34.

Name of the author : Kathryn H. Nightingale Title of the article : A novel ultrasonic technique for differentiating cysts from solid lesions: Preliminary results in the breast Title of the item : Ultrasound—in medicine and biology Date : 1995.

Name of the author : S. e. Masøy Title of the article : SURF imaging: In vivo demonstration of an ultrasound contrast agent detection technique Title of the item : IEEE Transactions on Ultrasonics, Ferroelectrics, and Frequency Control Date : May 2008 pp. 1112-1121.

Name of the author : Olaf T. von Ramm Title of the article : Real-time volumetric ultrasound imaging system Title of the item : Journal of Digital Imaging Date : Nov. 1990 pp. 261-266.

Name of the author : Shiota I Title of the article : Real-time three-dimensional echocardiography for determining right ventricular stroke volume in an animal model of chronic right ventricular volume overload Title of the item : Circulation Date : May 1998.

Name of the author : Gateau J Title of the article : In vivo bubble nucleation probability in sheep brain tissue Title of the item : Physics in Medicine and Biology Date : 2011 pp. 17.

Name of the author : J. Kuo Title of the article : Left ventricle function analysis with real-time three-dimensional ultrasound Title of the item : Engineering in Medicine and Biology Date : 2002 pp. 1105-1106.

Name of the author : Pellikka Title of the article : American Society of Echocardiography Cardiovascular Technology and Research Summit: A Roadmap for 2020 Title of the item : J Am Soc Echocardiogr Date : 2013.

Name of the author : B. F. Osmanski Title of the article : Ultrafast Doppler Imaging of Blood Flow Dynamics in the Myocardium Title of the item : IEEE Transactions on Medical Imaging Date : Aug. 2012 pp. 1661-1668.

(56) References Cited

OTHER PUBLICATIONS

Name of the author : Manolis Vavuranakis Title of the article : A new method for assessment of plaque vulnerability based on vasa vasorum imaging, by using contrast-enhanced intravascular ultrasound and differential image analysis Title of the item : International Journal of Cardiology Date : Oct. 30, 2008.

Name of the author : Olivier Couture Title of the article : Ultrafast Imaging of Ultrasound Contrast Agents Title of the item : Ultrasound—in medicine and biology Date : Nov. 2009 pp. 1908-1916.

\* cited by examiner

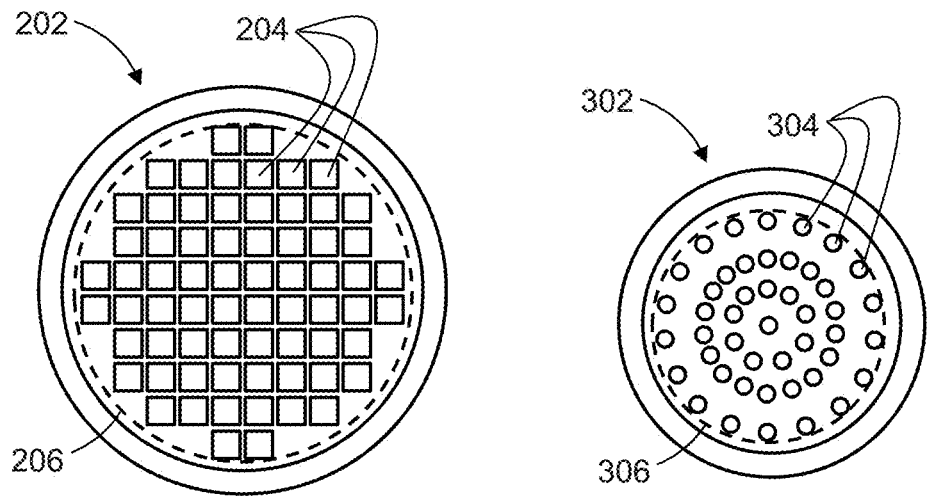
FIG. 2
FIG. 3
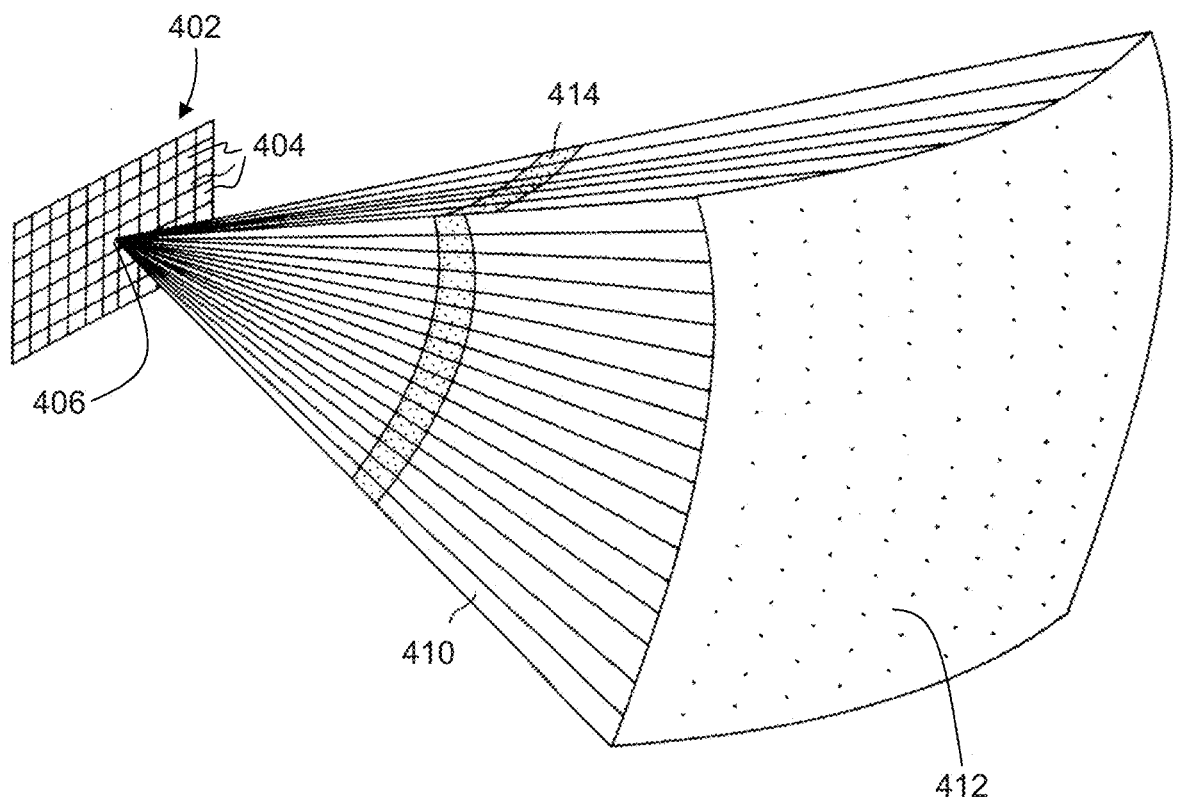
FIG. 4

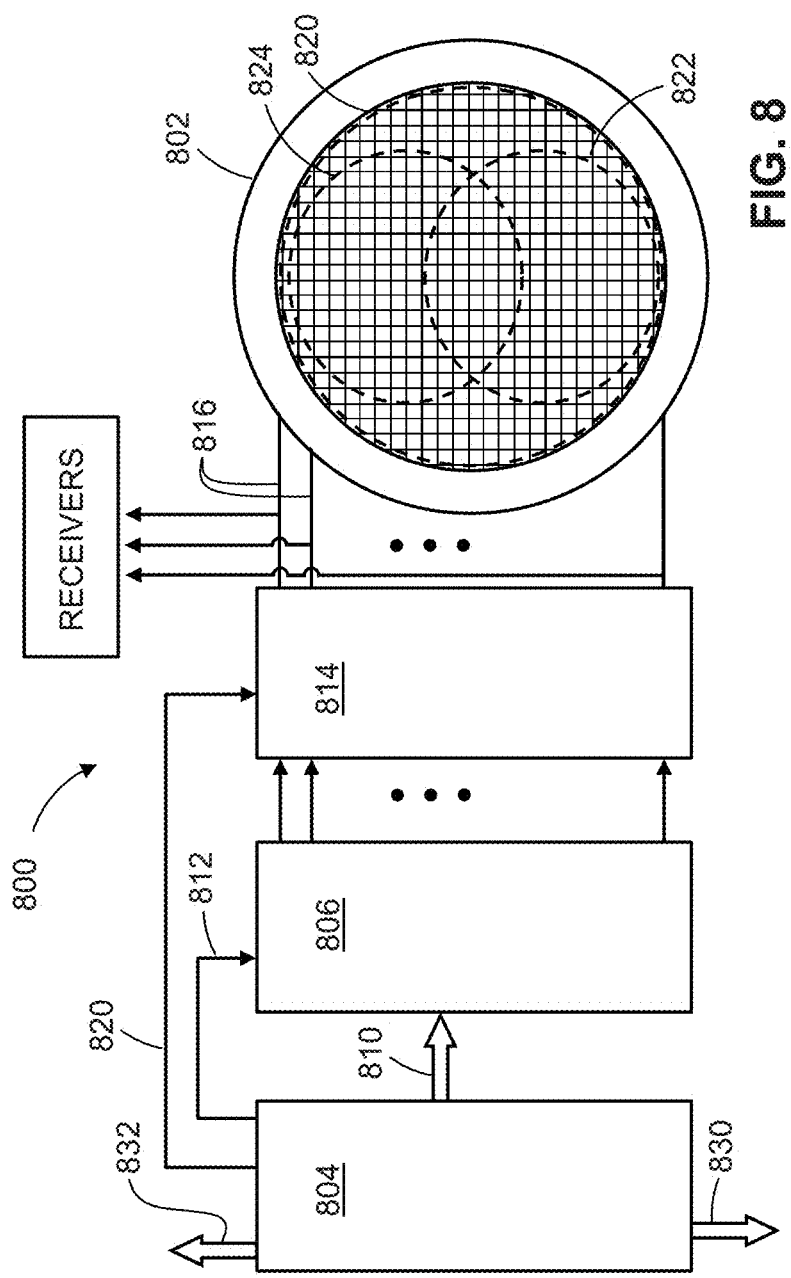

SYSTEMS AND METHODS FOR ULTRASOUND MOTION DISPLAY AND ANALYSIS

CROSS-REFERENCE TO RELATED APPLICATION

This application claims the benefit of priority of U.S. provisional patent application No. 62/079,024 titled "Systems and Methods for Ultrasound Motion Display and Analysis," filed on Nov. 13, 2014 which is incorporated herein in its entirety by this reference.

TECHNICAL FIELD

The present disclosure relates to ultrasound imaging. More particularly, the present disclosure relates to ultrasound imaging with high acquisition rates for clinical medical use.

BACKGROUND

Since its inception in the mid-1970s, real-time echocardiography employing phased array principles has had a significant impact on the practice of medicine particularly in cardiology. The real-time or live nature of image formation is one of the principal advantages of echocardiography next to its portability to the patient bedside and relatively low cost as compared with MRI and CT. Currently, live 2-D image scan rates of typical echocardiograms of 80° to 90° fields of view are 30 to 60 per second. These scan rates are adequate for many cardiac anatomical and functional diagnoses but are inadequate for studies of electromechanical coupling events in the heart. Electrical activity as measured by EKG should be sampled at rates of 500 Hz or greater for diagnostic purposes. To study the interaction of electrical and contractile events with comparable temporal resolution, imaging at 500 Hz (i.e., 500 frames per second) would be required.

There have been several studies in the recent past to increase ultrasound acquisition speeds As cardiac ultrasound is a pulse-echo imaging technique, the maximum frame rate (FR) achievable is ultimately limited by the speed of sound in tissue. For 1-D imaging techniques, such as A-mode or M-mode, the temporal sampling is determined by the maximum range being imaged. When extended to 2-D imaging, the field of view, or number of image lines acquired, must also be factored into the FR. For traditional pulse-echo B-mode imaging, the maximum achievable FR, and thus the maximum temporal sampling rate, is the inverse of the product of the time of flight for one transmit-receive operation and the total number of transmit-receive operations to generate one image. In conventional echocardiography, FR can only be increased by decreasing the resolution, the range, or field of view of the image. Scanning a volume further reduces the achievable imaging rates, in terms of volumes per second, since more look directions are needed to insonify and fully sample the volume. The volume can be thought of as consisting of a number of conventional B mode planes stacked one above the other. This stack defines the volume scanned and is the 3D field of view. Since multiple planes must be scanned 3D ultrasound scanning in adult echocardiography has been limited to about 20 volumes per second or less.

Three independent methods have been used to increase temporal sampling without significantly reducing image resolution and without a reduction of image size. The first method used to increase FR is parallel receive processing, known as exploso scanning. In exploso scanning, the transmit beam is broadened to insonify a larger area and multiple image lines are received from a single transmitted beam. This approach was first applied to echocardiography in 1984. Methods have been explored to broaden the transmit beam, including using a reduced transmit aperture, transmitting an unfocused beam, and defocused transmit beams. The acoustic pressure in the broadened beam may lower the echo levels and reduces the resolution in transmit. However, the overall resolution of the image may not be greatly affected if resolution in receive is maintained.

A second method uses multiple transmit beams, either at the same time or in quick succession. While this method provides an additional increase in FR, cross-talk between the simultaneous beams may lead to increased noise and potential artifacts in the resulting image. Recent work has described methods for reducing crosstalk between beams by various methods, including spatial separation, spectral separation or frequency multiplexing, and various apodization schemes. Crosstalk between beams may exist depending upon the shape (apodization) and separation of the beam. Such crosstalk may lead to image artifacts, such as bright targets appearing in multiple locations in the image. For a typical sector scanned image used in echocardiography acquired using a rectangular aperture array that maintains adequate sampling (i.e., sampled at least twice per diffraction limited resolution cell), the FR is given by:

$$FR = \frac{N_{Tx} \cdot N_{Rx}}{\left(2\frac{R_{max}}{c_{tissue}} + t_1 + t_3\right)\left(\frac{2FOV}{\sin^{-1}\frac{\lambda}{D}}\right) + t_2} \quad \text{(Equation 1)}$$

where $\lambda$ is the wavelength of sound in tissue, D is width of the rectangular aperture in the scanning plane, $R_{max}$ is the maximum range, and FOV is the desired sector field of view in degrees with the arcsine operation also in degrees. $N_{Tx}$ is the number of parallel transmit beams, and $N_{Rx}$ is the number of received image lines for each transmitted beam. Additional delays $t_1$ and $t_2$ represent the machine dependent turn-around time between sequential transmit-receive operations and between sequential frames, respectively. The third delay, $t_3$, is an additional delay added if multiple sequential transmit beams are temporally serialized. For conventional scanning, both $N_{Tx}$ and $N_{Rx}$ are 1, and $t_3$ is 0 seconds. For 3D scanning multiple planes separated from each other in the third dimension must be scanned so that the volume scan rate, VR, becomes VR=FR/P volumes per sec, where P is the number of planes scanned to provide the 3D field of view.

The third technique is gated image acquisition. In a gated system, the overall image sector is divided into M smaller sectors. Each small sector is imaged for one cardiac cycle at a higher rate using the patient's EKG signal as a timing reference. The overall image is then created by imaging over M cardiac cycles. This method provides an increase in temporal sampling by a factor of M, but not an increase in overall FR. This technique is sensitive to operator motion and patient motion, which lead to artifacts among the partial sectors. Due to the unpredictable nature of many arrhythmias, gated acquisition is not suited for hearts with arrhythmic events or irregular rhythm.

Using one or a combination of these methods, other investigators have recently studied high-acquisition-rate ultrasound imaging with post-acquisition image formation and display. These developments have not resulted in an instrument capable of live image formation; rather, image formation is off line, which is unsuitable for cardiac clinical imaging.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In at least one embodiment, a method of generating an image includes: emitting, by multiple ultrasonic elements of an array, multiple respective ultrasonic signals into a subject, the multiple respective ultrasonic signals defining at least two beam portions traveling in different directions; receiving, by the multiple ultrasonic elements, multiple respective ultrasonic echo signals; and generating at least one image of a portion of the subject from the received multiple ultrasonic echo signals.

In at least one example, wherein emitting, by multiple ultrasonic elements of an array, multiple respective ultrasonic signals into the subject includes emitting a negatively focused wavefront including the at least two beam portions traveling in the different directions.

In at least one example, emitting, by multiple ultrasonic elements of an array, multiple respective ultrasonic signals into the subject includes emitting a negatively focused wavefront having the at least two beam portions traveling in the different directions.

In at least one example, emitting, by multiple ultrasonic elements of an array, multiple respective ultrasonic signals into the subject includes emitting at least two negatively focused wavefronts, each including at least one of the at least two beam portions traveling in the different directions.

In at least one example, emitting at least two negatively focused wavefronts includes: sending a first negatively focused wavefront from a first subgroup of multiple ultrasonic elements of the array; and sending a second negatively focused wavefront from a first subgroup of multiple ultrasonic elements of the array.

In at least one example: the array defines an array aperture in which the multiple ultrasonic elements of the array are positioned; the first subgroup defines a first sub-aperture in which the multiple ultrasonic elements of the first subgroup are positioned; the second subgroup defines a second sub-aperture in which the multiple ultrasonic elements of the second subgroup are positioned; and the first sub-aperture and second sub-aperture as smaller than the array aperture.

In at least one example, the first and second sub-apertures overlap.

In at least one example, generating at least one image includes generating a video image in real time.

In at least one example, the method includes saving data including information about the multiple respective ultrasonic echo signals, and generating at least one image includes generating a video image using the saved data.

In at least one example, generating at least one image includes generating a selectable view-rate video image using the saved data.

In at least one embodiment, a system for generating an image includes: an array of multiple ultrasonic elements configured to emit multiple respective ultrasonic signals into a subject, the multiple respective ultrasonic signals defining at least two beam portions traveling in different directions, and to receive multiple respective ultrasonic echo signals; and a device configured to generate at least one image of a portion of the subject from the received multiple ultrasonic echo signals.

In at least one example, the array of multiple ultrasonic elements is configured to emit a negatively focused wavefront including the at least two beam portions traveling in the different directions.

In at least one example, the array of multiple ultrasonic elements is configured to emit a negatively focused wavefront having the at least two beam portions traveling in the different directions.

In at least one example, the array of multiple ultrasonic elements is configured to emit at least two negatively focused wavefronts, each including at least one of the at least two beam portions traveling in the different directions.

In at least one example, the at least two negatively focused wavefronts include: a first negatively focused wavefront from a first subgroup of multiple ultrasonic elements of the array; and a second negatively focused wavefront from a second subgroup of multiple ultrasonic elements of the array.

In at least one example: the array defines an array aperture in which the multiple ultrasonic elements of the array are positioned; the first subgroup defines a first sub-aperture in which the multiple ultrasonic elements of the first subgroup are positioned; the second subgroup defines a second sub-aperture in which the multiple ultrasonic elements of the second subgroup are positioned; and the first sub-aperture and second sub-aperture are smaller than the array aperture.

In at least one example, the first and second sub-apertures overlap.

In at least one example, the at least one image includes a video image in real time.

In at least one example, the system is configured to save data including information about the multiple respective ultrasonic echo signals, and wherein the at least one image includes generating a video image using the saved data.

In at least one example, the at least one image includes a selectable view-rate video image generated using the saved data.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 2 is a plan view of a planar array of ultrasonic elements arranged, according to at least one embodiment, in a rectangular grid pattern within a circular periphery FIG. 3 is a plan view of a planar array of ultrasonic elements arranged, according to at least one other embodiment, in a pattern of concentric circles within a circular periphery.

FIG. 4 is a perspective view representation of an ultrasonic signal propagating into a scan volume from a single transducer element in an array of multiple elements.

FIG. 8 is a diagrammatic representation of a system, according to at least one embodiment, by which an array of ultrasonic elements is effectively divided into subsections.

DETAILED DESCRIPTIONS

Figure 1:
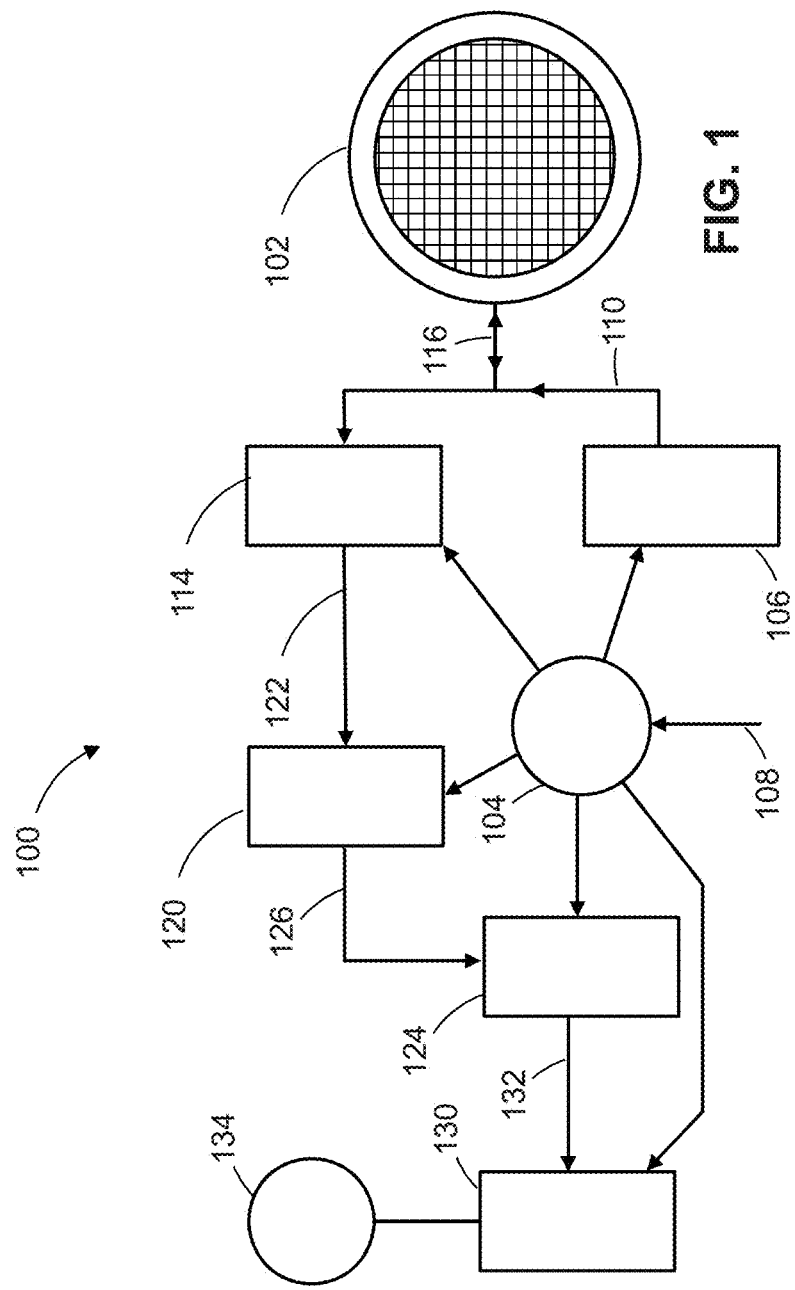
FIG. 1 is a diagrammatic representation of a system, according to at least one embodiment, by which ultrasonic beams are directed from an ultrasonic beam array.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

In the following descriptions, parallel processing is increased relative to previous approaches to facilitate the scanning rate of a volume by a factor of five or more as made possible by formation of a transmit beam that insonifies a larger volume by having a thousand or more look directions from each signal transmission or burst. In at least one embodiment, this is accomplished by emitting a negatively focused beam using the full available aperture space of an ultrasonic array and making the beam broad enough to include a high number of look directions. In at least one other embodiment, this is accomplished by dividing the array into subsections and concurrently or nearly concurrently using the subsections to emit negatively focused beams each allowing many look directions. Blood flow can be visualized by subtracting high speed images or implementing filters to accentuate certain motions in the heart or blood for volume scans and 2 D scans. High speed scans refer to imaging speeds above 150 per sec or faster and 100 volumes/sec or faster. This invention extends the application of B-Mode ultrasound imaging to higher speeds than was before available by using an unfocused or negatively focused ultrasound beam in conjunction with parallel receive processing to significantly increase scanning speeds. To analyze the rate of motion of tissues such as blood or cardiac muscle with the living body sequentially obtained high speed images may be added or subtracted with different weights to implement temporal filtering. Temporal filters will then permit the display of either slow, fast, or a range of motions of tissues depending on the selection of filter characteristics of the operator. The output of the filter system can also be measured and thus be quantified in a yet different display. An array of ultrasound transducer elements accomplishes realization. This array of elements within the transducer aperture may have various configurations including 1D, 2D or 3D configurations. The transducer array is connected to a number of transmitters which electrically excite the transducer elements. There may be as many transmitters as array elements, as in at least one embodiment, or fewer. Transmitters produce mono or biphasic pulses, pulse trains, or multiple pulse trains. Received signals from the tissue structures arising at each receive element are amplified and the outputs from the amplifiers are then sent to the parallel receive processing system which permits the simultaneous processing of receive signals from multiple directions.

These multiple directions are usually within the unfocused or negatively focused transmit beam. Transmit beam formation may be controlled by hardware, software or a combination of both. An unfocused or negatively focused transmit beam from the entire aperture is used to acquire ultrasound images in at least one embodiment. Beam formation in receive may use either coherent summation, short lag time correlation processing or some other means to uniquely steer the beam using each of the parallel signal paths. All echo information from each parallel receive processing unit is envelope detected and then digitally sampled and stored in a memory together with the spatial coordinates of the acquisition direction of each of the parallel beams. Multiple parallel acquisitions may be used to capture one entire ultrasound image depending on the required field of view. Image data stored in the memory is periodically sent to the display system after the scan conversion to permit real time visualization of the target such as blood. In general, the rate of such images display is governed by the display system (monitor), generally slower than the ultrasound acquisition rate. To gain appreciation of higher speed motion, images are displayed in slow motion. In this way all the acquired high speed image data can be visualized. The stored image data can now be digitally filtered prior to display to enhance certain motion speeds of the tissue. This serial images temporal processing of high speed ultrasonic data is new and advantageous. Depending on the desired filter response, e.g. high pass, low pass, band pass, sequential images may be added or subtracted with varying weights to form the final image. For example, images may be subtracted to eliminate stationary structures and to enhance very fast moving structures. The ability to filter a sequence of high speed images enhances fast motion imaging in cardiac structures during the contractile phase of the heart and to identify small vasculature normally not seen with conventional imaging. The speed of conventional ultrasound imaging is limited to 60-100 frames per second. This speed of imaging is below the accepted physiological temporal resolution required for accurate assessments of cardiac and other organ motion. Physiological events occur at 1 to 5 millisecond intervals. The ultrasound high speed imaging system described herein acquires images at rates of 500 to 1000 frames per second (1 to 2 milliseconds) in some embodiments. These speeds permit temporal spatial processing of images to enhance components of motion not normally seen. Such imaging also allows the visualization of blood flow within vessels. The new system described herein will permit more accurate quantitation of cardiac ventricular motion, such as strain analysis. Other application may include visualization of flow fields in 2D and 3D, delineation of small vessels in 2D and 3D and the organ perfusion distribution in space and time.

In at least one example, elements in an array are divided into two subgroups within two sub-apertures. A first subgroup of elements is used to emit a beam with five hundred look directions from a first sub-aperture and simultaneously a second subgroup of elements is used to emit a beam with five hundred look directions from a second sub-aperture. A thousand beams are thus effectively formed using the sub-apertures. Combinations of these examples are within the scope of these descriptions.

A system 100 includes an ultrasonic array 102 of elements by which ultrasonic beams are directed into a scan volume in use. In at least one embodiment, the system 100 includes a timing and control module 104 that operationally controls the functions of transmit-side and receive-side devices. A transmit-side controller 106 sends activation signals to the ultrasonic array 102. Input 108 to the timing and control module 104 in FIG. 1 represents user inputs and/or data and inputs from other equipment. The signal line 110 from the transmit-side controller 106 toward the ultrasonic array 102 represents as many independent signal lines as needed to individually activate each element of the array or as needed to ultimately control each element independently or in subgroups. The signal line 110 continues to the receive-side amplifier device 114 where processing of the receive signals emanating from the transducer elements of the array begins. In various examples: the elements of the array 102 are used for both transmit and receive; some of the elements are used for transmit and some are used for receive; some are used for both transmit and receive, others are used for only transmit, and others yet are used for only receive; and all such examples may change over time such that any or all elements functions as to transmit, receive, or both can be re-assigned at any time.

Bidirectional communication of activation signals to the ultrasonic array 102 and the receive signals emanating from the transducer elements of the array is conducted by a line 116 in communication with the signal line 110 upstream of the receive-side amplifier device 114. The pre-processed receive signals are passed to a receive-side delay device 120 downstream of the receive-side amplifier device 114 via a line 122. A multiplexer may be used for example between the transmit-side controller 106 and the array 102, and/or between the array 102 and receive-side amplifier device 114. The line 116 in FIG. 1 may include or represent a multiplexer.

The receive-side delay device 120 facilitates the discrimination of the response of each scan volume location from the response of every other location so as to facilitate the generation of a three-dimensional mapping of the scan volume for imaging purposes. As the array 102 sends outgoing ultrasonic signals into a scan volume, incoming ultrasonic echo signals return to the array 102 causing the generation of receive signals in the elements of the array. As the time of flight, for both send and return signals, from any particular scan volume location varies from element to element in the array, the return signals cause a time-varying receive signal at each element. The receive-side delay device 120 can time shift or time stamp the pre-processed receive signals downstream of the receive-side amplifier device 114 to compensate for the time-of-flight (TOF) variations between each element and each scan volume location. By introducing a delay into the receive signal train of each element according to the time-of-flight between that element and a particular scan volume location, the return signal portions corresponding to that particular scan volume location can be identified.

A downstream real-time processor and detection device 124 gets the receive signals from the receive-side delay device 120 via a line 126. A spatial and temporal image processing device 130 receives data from the device 124 via a line 132 and further processes the data and outputs images on a display. For example, constant response signal level associated with a particular scan image location can be subtracted so as to reveal movement in lieu of stationary features. Images can be produced in real time from data slices for immediate clinical use and to assure that an intended subject is within the scan volume. The device 124 and/or spatial and temporal image processing device 130 include or are in communication with a storage device that stores the data stream. The saved data can later be used to create motion videos at selectable view rates so the scan volumes can be viewed at any selected speed to facilitate viewing and analysis of features moving in slow (fast video)

and fast (slow video) time regimes. That is, the data can be later used to generate fast and slow motion videos.

The array 102 of FIG. 1 is shown with a fill pattern generically representing many ways in which multiple elements can be arranged within an effective aperture. The fill pattern represents many element arrangement patterns in many embodiments.

FIG. 2 is a plan view of a planar array 202 of elements 204 arranged, according to at least one embodiment, in a rectangular grid pattern within a circular periphery 206 defining an effective circular aperture of the array.

FIG. 3 is a plan view of a planar array 302 of elements 304 arranged, according to at least one other embodiment, in a pattern of concentric circles within a circular periphery 306 defining an effective circular aperture of the array. Many other element arrangements by which the array of FIG. 1 may be constructed are within the scope of these descriptions. The patterns by which the elements are placed of distributed in FIGS. 2 and 3 are examples. Many other placement patterns are within the scope of these descriptions. There are many ways to spatially arrange elements in an array or multiple elements within the scope of these descriptions.

FIG. 4 is a perspective view representation of an ultrasonic signal propagating into a scan volume from a single transducer element in an array 402 of multiple elements 404. Although illustrated as having a rectangular periphery in the drawing, the array 402 of FIG. 4 could have any other outer peripheral shape, such as circular as shown for the arrays in FIGS. 2 and 3, and any arrangement pattern of elements. A single transducer element 406 is shown in FIG. 4 to emit an ultrasonic signal 410 that advances forward from the array. In a medium having a uniform speed for the propagation of sound, the signal 410 can be said to have a diverging wavefront 412. In theory a diverging spherical wavefront 412 is generated as all points in the scan volume equidistant from the active transducer element 406 in a spherical shell slice 414 receive the signal simultaneously. By use of multiple elements in the array, the wavefront of the advancing signal can be manipulated. When all or some portion of the many elements in the array are used, each contributes to a resulting beam formed by the summation of the many signals including constructive and destructive interference.

Figure 5:
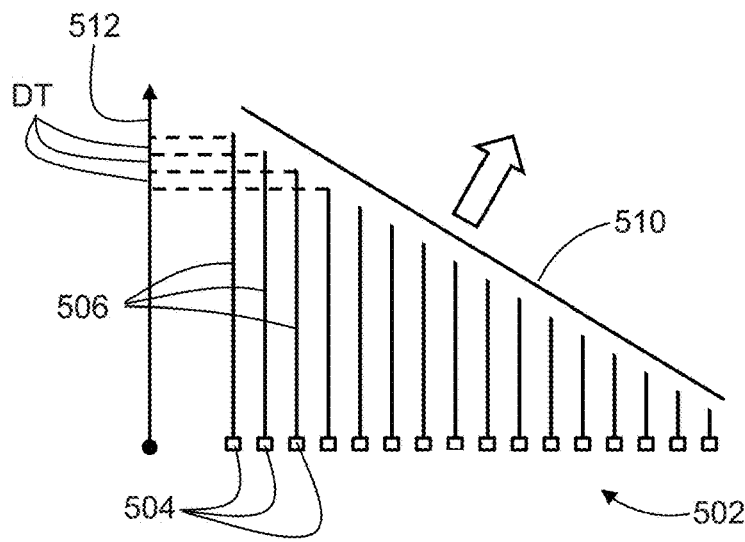
FIG. 5 is a side view representation of an ultrasonic signal propagating as a planar wavefront into a scan volume from multiple transducer elements in an array of multiple elements.

FIG. 5 is a side view representation of an ultrasonic signal propagating into a scan volume from multiple transducer elements 504 in an array 502 of multiple elements. The elements emit respective signals with a constant time delay interval DT between adjacent elements firing in succession from left to right. A wavefront 510, to which each active element contributes by interference, advances from the array. The respective propagation distance 506 of the signal of each element to the resulting wavefront is proportional to the time of flight (TOF) of the signal from that element. Thus, those elements to the left in FIG. 5, which activated earlier than those to the right as represented by a TOF axis 512, have corresponding longer propagation distances. Where each element in FIG. 5 represents a row of elements in a 2D array, the resulting advancing interference pattern can be said to have a wavefront that is approximately planar, at least near the array and not accounting for edge effects, due to the constant time delay interval DT between adjacent rows, and can be said to be a beam directed to the right in FIG. 5, due to the firing of the rows in time succession from left to right.

Figure 6:
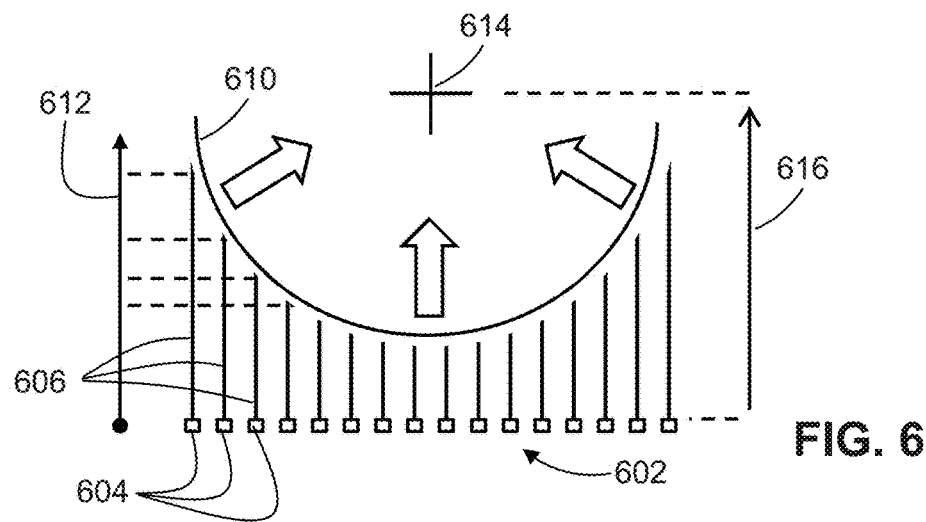
FIG. 6 is a side view representation of an ultrasonic signal propagating as a concave or converging spherical wavefront defining a focused beam.

FIG. 6 is a side view representation of an ultrasonic signal propagating into a scan volume from multiple transducer elements 604 in an array 602 of multiple elements. The respective propagation distance 606 of the signal of each element to the resulting wavefront is proportional to the time of flight (TOF) of the signal from that element. As in FIG. 5, the elements 604 emit respective signals with respective time delays, however, in FIG. 6 peripheral elements are activated earlier than central elements and the time delays represented by the TOF axis 612 are chosen to generate a concave bowl-shaped wavefront 610. Where each element in FIG. 6 represents a circular pattern of elements in a 2D array centered around the minima point in the illustrated wavefront 610, the resulting advancing interference pattern can be said to be a concave spherical wavefront converging upon a focal point 614 forward of the array. This defines a focused beam having a focal point at a positive distance 616 from the array.

Figure 7:
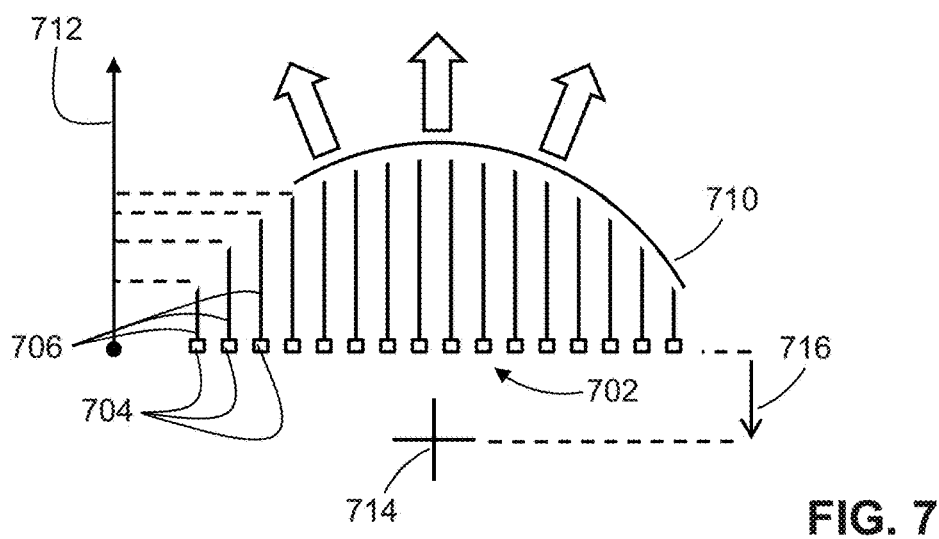
FIG. 7 is a side view representation of an ultrasonic signal propagating as a convex or diverging spherical wavefront defining a negatively focused beam.

FIG. 7 is a side view representation of an ultrasonic signal propagating into a scan volume from multiple transducer elements 704 in an array 702 of multiple elements. The respective propagation distance 706 of the signal of each element to the resulting wavefront is proportional to the time of flight (TOF) of the signal from that element. As in FIG. 6, the elements 704 emit respective signals with respective time delays, however, in FIG. 7 central elements are activated earlier than peripheral elements and the time delays represented by the TOF axis 712 are chosen to generate a convex-shaped wavefront 710. Where each element 704 in FIG. 7 represents a circular pattern of elements in a 2D array centered around the maxima point in the illustrated wavefront, the resulting advancing interference pattern can be said to be a convex spherical wavefront 710 diverging from a focal point 714 behind the array. This defines a negatively focused beam having a focal point at a negative distance 716 from the array.

A defocused beam in these descriptions refers to a negatively focused beam, that is, a beam having a focal point or multiple focal points defined rearward of the array relative to a scanned volume. An unfocused beam refers to a beam of long focus (such as one thousand cm), that is, a beam having a focal point defined forward of the array and deep within a scanned volume or beyond.

In FIGS. 6 and 7, by introduction of a constant delay or advance in the activation times of the elements throughout the array, the focal point can be adjustably positioned relative to the array plane in which the elements reside. For example, an additional delay moves the focal points further forward, and an advance or reduced delay moves the focal points backwards. Thus, FIGS. 5-7 demonstrate that a beam can be shaped and directed according to a schedule of activation of the elements in an array. As described with reference to FIGS. 8-10, by zone control or subgrouping of element sets in a single array device into effective sub-arrays, a single beam array can as well be used to generate multiple beams, each having its own beam shape characteristics and propagation direction.

FIG. 8 is a diagrammatic representation of a system 800, according to at least one embodiment, by which an array 802 of ultrasonic elements is effectively divided into subsections each of which emits beams from effective sub-apertures into a scan volume in use. In at least one embodiment, the system 800 includes master timing and control module 804 that operationally controls the functions of transmit-side and receive-side devices. A transmit-side controller 806 receives data 810 and a clock signal 812 from the master timing and control module 804 and sends element-specific commands to a transmitter interface device 814, which sends activation signals to the ultrasonic array 802 by which each element thereof is controlled independently or in subgroups. The signal lines 816 from the transmitter interface device 814 toward the ultrasonic array 802 represent as many independent signal lines as needed to activate each element of the array independently or in subgroups, or a multiplexer could be employed with less or any number of physical communication lines. The signal lines 816 further communicate with receivers, for example as shown as the receive-side amplifier device 114 in FIG. 1, where processing of the receive signals emanating from the transducer elements of the array begins. The lines 816 in FIG. 8 may include or represent a multiplexer. One or more multiplexers can be included with or within the transducer device 802.

The master timing and control module 804 sends aperture select data 820 to the transmitter interface device 814 to control sub-aperture selection so as to effectively divide the array 802 into subgroups of elements. Three selections for concurrent or independent use, or use in any combination are shown for example in array 802 of FIG. 8. A full aperture selection 820, and two sub-aperture selections 822 and 824 defining respective subgroups of the elements are shown. Data connections 830 and 832 sending data from the master timing and control module 804 to delay and image control devices are also shown in FIG. 8, of which further descriptions are made in the preceding, for example with reference to FIG. 1.

Figure 10:
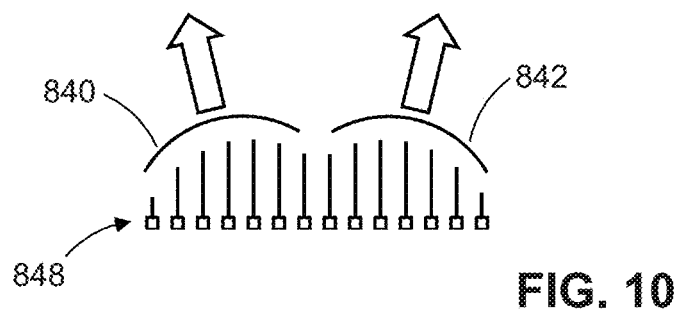
FIG. 10 is a side view representation of an ultrasonic signal propagating as two negatively focused beams moving simultaneously in different directions.
Figure 9:
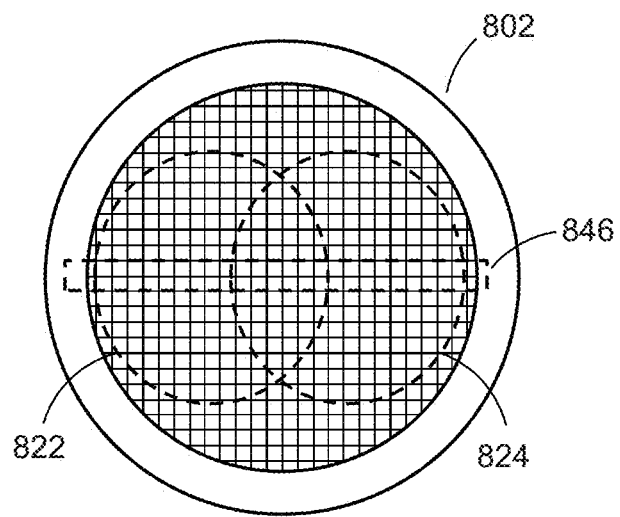
FIG. 9 is a plan view of the array of FIG. 8, showing an array slice corresponding to elements in FIG. 10.

In the illustrated selection examples, all of the elements of the array are within the full aperture selection 820 and could be used, for example, to generate a wide aperture negatively focused beam as shown in FIG. 7. The element subgroups within sub-aperture selections 822 and 824 in FIG. 8 could be used, for example, to generate the negatively focused beams 840 and 842 shown as directed in different directions in FIG. 10. The array elements in FIG. 9 along the array slice 846 are represented as elements 848 in FIG. 10, showing that the sub-aperture selections 822 and 824 are being used to generate the two negatively focused beams 840 and 842 in FIG. 10 simultaneously. In other examples within the scope of these descriptions, multiple beams are sent from multiple subgroups of elements at different times. Furthermore, the sub-aperture selections 822 and 824 are shown in FIGS. 8 and 9 as having lesser effective aperture dimensions than the full aperture selection 820, and are shown as overlapping. The corresponding element subgroups are defined as all elements within the sub-aperture selections, and thus those elements within the area where the two selections 822 and 824 overlap are included in both subgroups. In other examples, multiple non-overlapping sub-aperture selections 822 are made and no elements are shared by the defined subgroups. In yet other examples, subgroups are defined to populate any sub-aperture area or even the full aperture of the array, such that, for example, multiple subgroups can be defined with partially or entirely overlapping subgroup-apertures with or without sharing any of their elements. Furthermore, the positively and negatively focused beams shown respectively in FIGS. 6, 7 and 10 are described as having spherical wavefronts, however these descriptions relate as well to other wavefront configurations for both positively and negatively focused beams in any number. For example, in at least one embodiment a negatively focused parabolic beam diverges outward from an array, and in another embodiment, multiple negatively focused parabolic beams are generated. Multiple negative focal points may be used, and multiple beam shapes may be used with one or more than geometric focal points. Thus, many variations may be used.

By the above descriptions, parallel processing can increase, relative to previous approaches, scanning rates of a scan volume by having multiple look directions in each signal transmission or burst from an ultrasonic array. This can be accomplished by emitting a negatively focused beam using the full available aperture space of an ultrasonic array and making the beam broad enough to include a high number of look directions. This can be accomplished by dividing the array into subsections and concurrently or nearly concurrently using the subsections to emit defocused beams each corresponding to many look directions. All combinations of the above examples are within the scope of these descriptions.

The following descriptions relate to a new high-speed system, within the scope of the above descriptions with reference to FIGS. 1-9, that is capable of live imaging while acquiring images at rates up to 1000 frames per second for adult cardiac imaging, and up to 2500 per second for other applications (e.g., pediatric echocardiography). Transmit configurations are described, and examples of clinical images are shown. In practical clinical use of echocardiography, it is preferable for the clinician or technician to be able to view live images as they are acquired to ensure that the anatomy of interest is scanned. While the acquisition rates achieved in the following descriptions generate information in excess of what a human operator may discern while data is collected, high temporal resolution images and the simultaneously acquired EKG signals can be studied retrospectively in slow motion or frame by frame.

In at least one embodiment, an ultrasound scanning system is used to acquire, display, and store all images, and to permit real-time 3-D volumetric imaging. The ultrasound scanning system is highly flexible and features 512 independently controlled transmitters with a delay accuracy of ±2.5 ns. Each transmitter can be programmed for amplitude, center frequency, bipolar pulse length, and pulse bandwidth. In addition, each transmitter can transmit up to 8 separate and independent pulses in rapid succession for near simultaneous transmit applications.

In at least one embodiment, there are 1024 receive channels with 9 MHz bandwidth that are digitized at 50 MHz. The output from each of the 1024 channels is then sent to 32 beamformers for a total count of 32,768 hardware beamformers in the system.

In at least one example as described in the following, a 96-element linear array is used, employing 3072 beamformers. The output of all unused beamformers is turned off. The architecture of the system permits software controlled selection of the number of active transmit and receive channels. The receive system is self-calibrating so that the signal amplitude at the detectors is independent of the number of transducer elements used.

The array used has an active aperture of 21 mm width and 14 mm height, and a center frequency of 3.5 MHz. The output of the beamformers is distributed to 32 software programmable detectors. Amplitude of the detected signal can be adjusted and various time domain filters can be implemented via software. The 15-bit detected brightness data from each 32 independent detectors along with temporally synchronous EKG data are transferred to a computer, such as a PC, for display and storage via three CameraLink connections. The output of the detectors is transferred at a measured rate of up to 1.35 Gbps.

The computer is outfitted with three DALSA X64 Frame-Grabber cards: two for dedicated image data acquisition with the third acquiring EKG data and various other parameters. Display and storage of this data are accomplished by software. High-speed transfers and basic image processing are performed in real time by the Intel Integrated Performance Primitives libraries. Real-time display of ultrasound images is performed using Microsoft DirectX libraries.

During live clinical scans, images are displayed as in conventional clinical echocardiography. When high-speed imaging function is selected, the display system shows images at the native rate of the video system, but all image data are immediately available for analysis and real-time display. All images are stored in a circular frame buffer in the computer memory with a capacity of 25,000 frames. At 1000 fps, this memory capacity permits storage of up to 25 seconds of images. These images can be played back at slower playback rates (i.e., in slow motion, or frame-by-frame as selected by the operator). Various image parameters such as brightness, gamma, and contrast can be adjusted during playback mode, and various temporal and spatial filters can be applied.

A transmit beam configuration, according to at least one embodiment, includes a phased array scanner system. In at least one example, the system is capable of 32 to 1 parallel receive processing. The transmit beam in at least one example is widened to at least 16° to accommodate 32 received image lines spaced every 0.5°. The diffraction limited resolution of a 21-mm wide transducer used at 3.5 MHz is 1.2°. For this transducer, the transition distance is approximately 30 cm. To avoid the self-focusing effect (i.e., the natural narrowing of the beam), the beam profile can be generated when transmitting a negatively focused beam at minus 30 cm. For comparison, a transmit focused at mid-range (7 cm) and a beam focused at 1,000 cm (the unfocused beam) can also be measured. The f-number in receive varied from 1 to 6.5 depending on depth. No amplitude apodization was implemented in transmit or receive, nor was spatial or temporal compounding employed.

For each transmit scheme, beam plots are measured by clamping the transducer to a ring stand in a water tank. An OndaCorp HGL-0200 hydrophone is attached to a custom rotational stage with the center of rotation aligned to the center of the array transducer. Peak-to-peak receive voltage from the hydrophone is measured with an oscilloscope (Agilent DSO06054A, Agilent Technologies Inc., Santa Clara, Calif., USA) at 10 intervals over a field of view from −35° to +35°. Measurements are made every 2 cm, from 3 cm to 13 cm in range. At each range, the hydrophone's location is centered on axis in both azimuth and elevation by translating the hydrophone until the maximum receive voltage is measured. The transmit beam is focused at the range being measured during the centering process. Measurements are then made using the three transmit beams.

To visualize the appearance of the ultrasound beams as a function of distance from the transducer, a synthetic sponge with regular cell spacing in a water tank can be scanned. A B-mode image of the transmit beam pattern can be produced by transmitting on axis, at 0°, while receive beamformers are steered in the usual fashion over the sector field of view. For such images, the transducer can be manually held at the edge of the sponge. Images can be obtained and recorded with unfocused, defocused, and focused beams.

To quantify image quality for high FR imaging, both spatial resolution and image contrast are measured. Spatial resolution is determined by imaging an AIUM standard resolution phantom. The phantom contains wires spaced at 1, 2, 3, and 4 mm apart in the center. The linear array described previously is clamped in a fixed position and the phantom is aligned so that the resolution targets are located near the focal point of the focused transmit beam, at 70 mm depth. Images are acquired with focused, unfocused, and defocused transmit beams, acquiring two image lines for each transmitted acoustic pulse to achieve a target FR of 60 Hz as is typical in clinical practice. A fourth image is acquired using the same settings as when scanning at 1000 fps, using a defocused transmit beam and receiving 32 images lines for each transmitted pulse.

The contrast ratio can be measured by imaging a tissue-mimicking phantom (CIRS Model 040GSE Multi-Purpose Multi-Tissue Ultrasound Phantom. A central region of the phantom that contains a 0.5-cm-diameter anechoic void can be imaged four times, once for each of the three transmit schemes with two image lines received per transmitted pulse, to achieve an FR of 60 Hz. The fourth time, the phantom can be imaged at 1000 fps with a defocused transmit and 32 image lines received for each transmit. The average brightness of a 5-by-5 region of samples within the void can be calculated over 60 frames; likewise, the average brightness of an 11-by-11 region of samples in the tissue-mimicking region (i.e., speckle pattern) can be taken over 60 frames. The ratio of these two values can calculated to give the contrast ratio.

EXAMPLE STUDY—In one example in adult cardiac imaging, seventy volunteers had standard chest wall echocardiograms performed at rates up to 1000 frames per second with 800 FOV and 14-cm range. Volunteers enrolled in this study ranged from 18 to 81 years old, these volunteers consisted of a combination of healthy individuals with no previous diagnosis of cardiac disease and patients who already had a physician-ordered echocardiogram performed. All volunteers consented, and all human studies were performed under IRB approval. During the examination, patients had a lead I EKG acquired synchronously with the image acquisition. Lead placement and ultrasonic exams were performed by licensed sonographers. During the examination, volunteers were supine on an examination table and, if necessary to expose a more viable acoustic window, were instructed to roll on their left side. Images were acquired in up to five standard views: parasternal long axis (PLAX) and short axis (PSAX), and apical four-chamber (AP4), two-chamber (AP2), and three-chamber (AP3) views. In the example, images were obtained at the same power level outputs, which was about 50 mW/cm$^2$.

Figure 11:
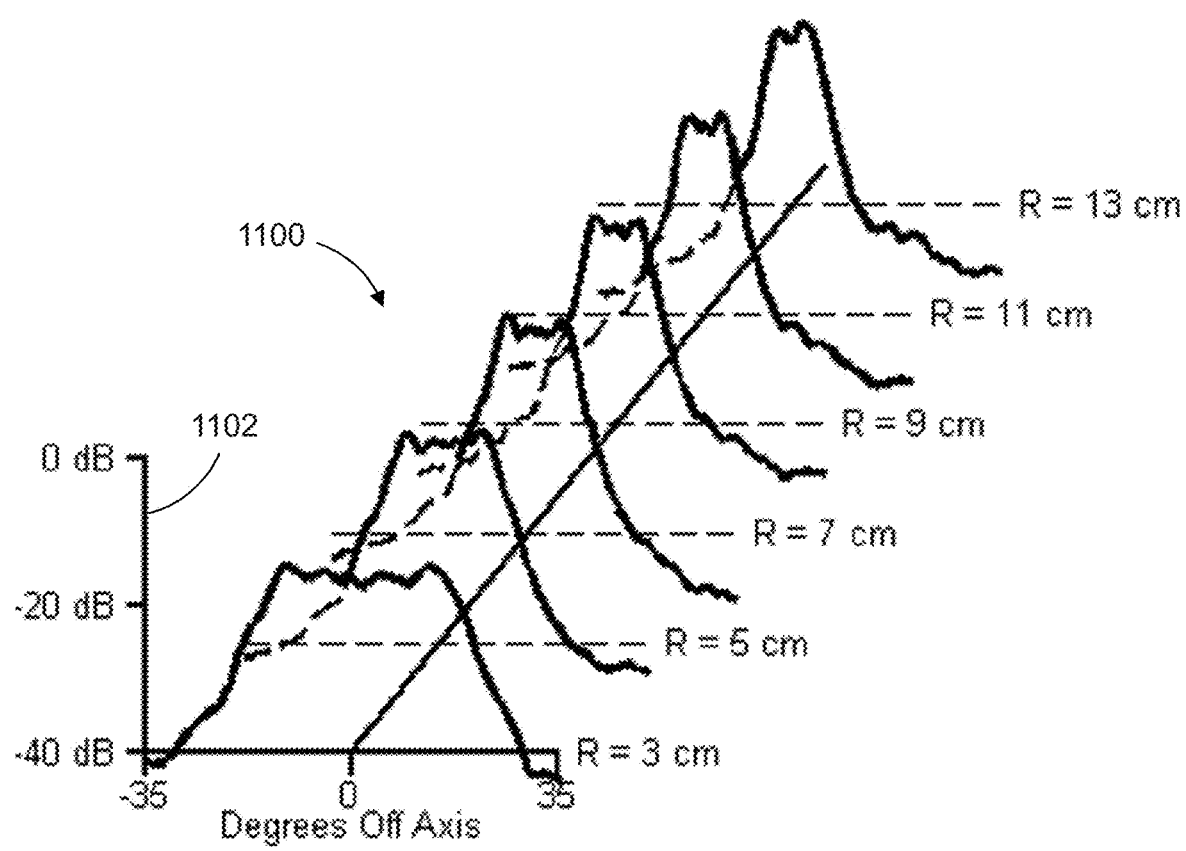
FIG. 11 is a measured beam plot for an unfocused transmit beam.
Figure 12:
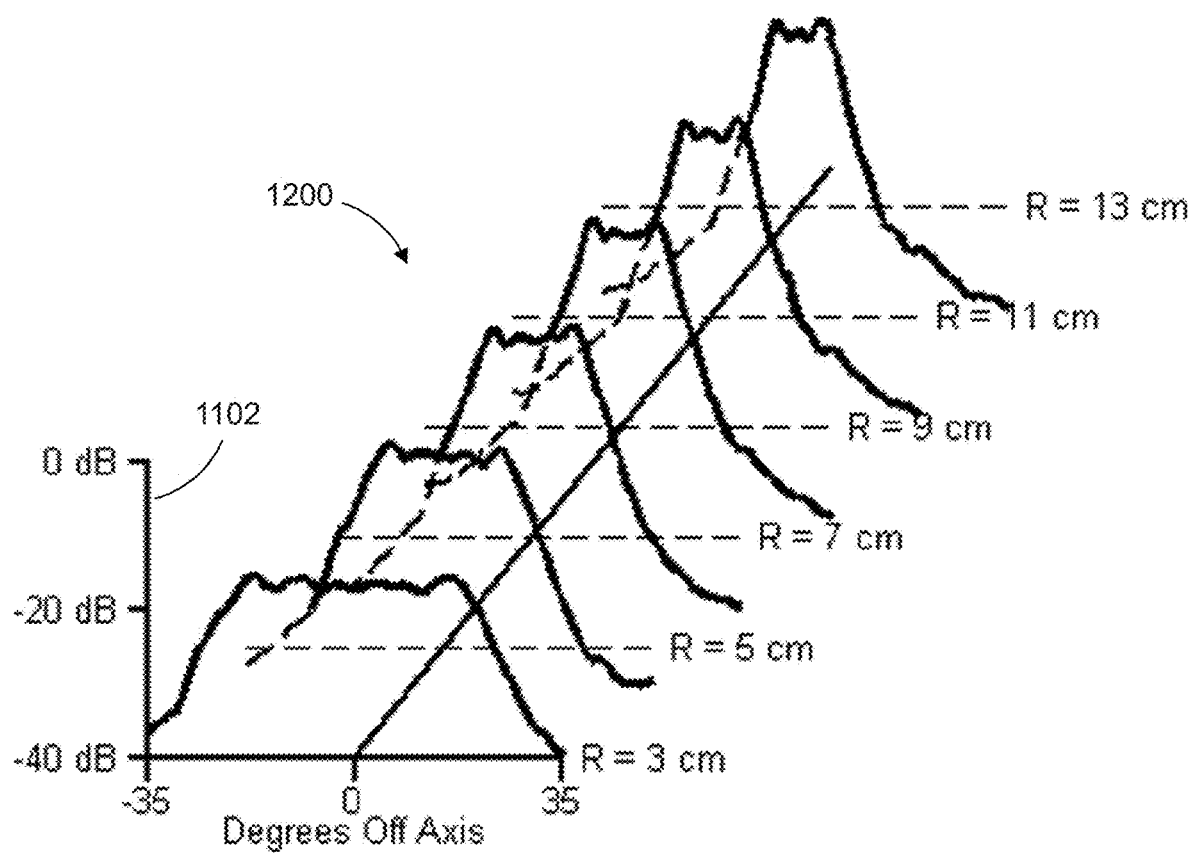
FIG. 12 is a measured beam plot for a transmit beam with −30 cm focus.
Figure 13:
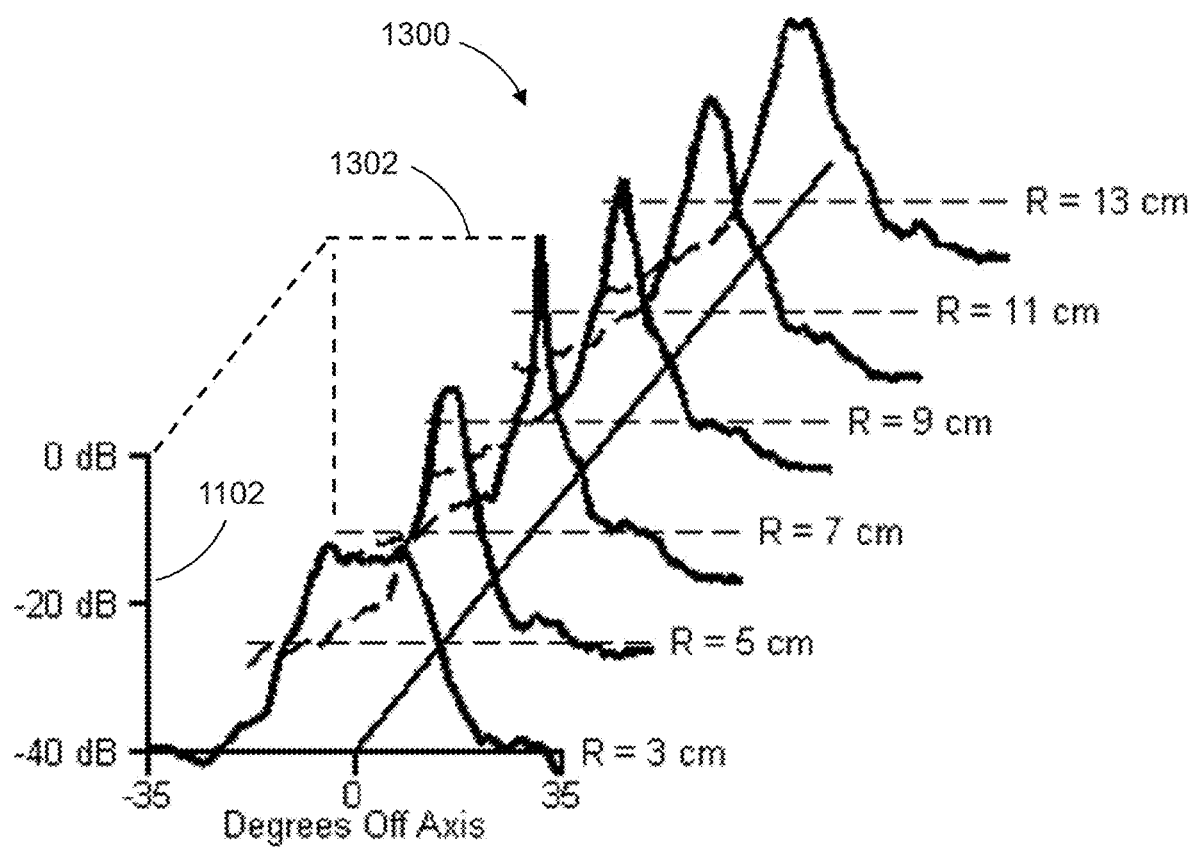
FIG. 13 is a measured beam plot for a transmit beam focused at 7 cm.

BEAM PLOTS—The array used both in vitro and in vivo was a linear array with 96 elements, 21-mm aperture in the scan plane (azimuth), height of 14 mm (elevation), and center frequency of 3.5 MHz. Beam plots measured for each transmit scheme are shown in FIGS. 11-13. FIG. 11 is a measured beam plot 1100 for the unfocused transmit beam. FIG. 12 is a measured beam plot 1200 for the transmit beam with −30-cm focus. FIG. 13 is a measured beam plot 1300 for the transmit beam focused at 7 cm.

The received voltages are displayed (FIGS. 11-13) on a decibel scale y-axis 1102, using the maximum of all measurements as the reference voltage. The reference voltage at 0 dB as shown in FIG. 13 corresponds to the peak voltage 1302 measured at the 7-cm range for the focused transmit. The amplitude of each beam plot at different ranges can be measured by using the receive amplitude scale on the y-axis 1102 on the left of the 3-cm range plot. The diagonal line in FIGS. 11-13 indicates the intersection of the −40-dB amplitude at 0° off axis at each range. The dashed horizontal lower lines indicate the −40-dB level for each measured range.

As can be seen from the beam plots in FIGS. 11-13, the location of the focal point greatly affects the profile of the transmitted acoustic beam. In the case of the unfocused transmit seen in FIG. 11, the beam consistently converges over all measured ranges. As the transducer is diffraction limited, the transmitted beam naturally focuses at the transition distance, which, given the size of the aperture and wavelength transmitted, is approximately 30 cm for this transducer.

The defocused transmit in FIG. 12 also converges, albeit not as rapidly as the unfocused beam. Over the measured range, the negatively focused beam is consistently the broadest, but at the expense of ripple in the main lobe and reduced overall amplitude. For this case, the negative focus is analogous to placing a diverging lens on the aperture. A negative focus near the transition distance reduces the self-focusing effect of the aperture for the range being imaged.

For the focused case in FIG. 13, the beam has already begun to converge at a range of 3 cm and continues to narrow until the focus is reached at 7 cm. Beyond the focus, the beam diverges. The peak amplitude at each range also increases to its peak at 7 cm and decreases at further ranges as the beam spreads out.

The three transmit beams presented here were compared quantitatively in terms of average beam width, amplitude, and amplitude ripple over the 3-cm to 13-cm range. The −6-dB beam width averaged over all ranges was found to be 6.8±5.4° for the focused transmit beam, 16.0±8.3° for the unfocused, and 22.6±11.1° for the defocused case. A second metric is the average reduction in peak amplitude, at each range, with respect to the maximum amplitude at the 7-cm range for the focused transmit beam (FIG. 13). For the focused case, this is a metric of variation in amplitude of the beam over 13 cm, whereas for the other two transmit schemes (FIGS. 11, 12), this is a measurement of loss in signal with respect to a focused transmit beam. The average reduction was found to be −8.6±5.0 dB for the focused transmit, −2.7±1.8 dB for the unfocused, and −13.3±1.5 dB for the defocused beam. A third comparison was the ripple in the main beam, or the difference in the maximum and minimum voltages measured in the main lobe of each transmit beam. For the focused transmit, the ripple was found to be 0.6±0.9 dB, for the unfocused 2.7±0.2 dB, and for the defocused 2.4±0.4 dB.

Figures 14A, 14B, 14C:
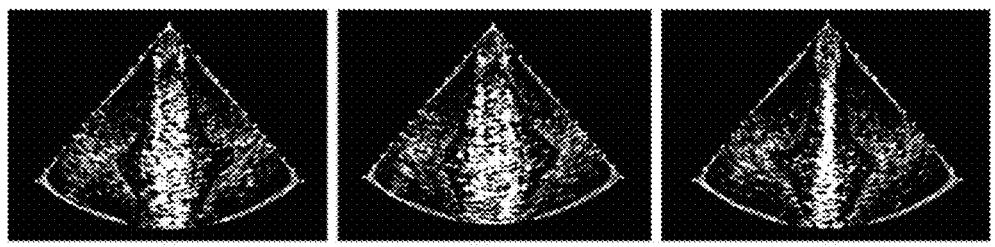
FIG. 14A is a speckle target image demonstrating the relative beam width for an unfocused transmit beam.
FIG. 14B is a speckle target image demonstrating the relative beam width for a transmit beam with −30 cm focus.
FIG. 14C is a speckle target image demonstrating the relative beam width for a transmit beam focused at 7 cm.

Qualitative differences between beam profiles can be seen in beam images in FIGS. 14A-14C. FIG. 14A is a speckle target image demonstrating the relative beam width for the unfocused transmit beam. FIG. 14B is a speckle target image demonstrating the relative beam width for the transmit beam with −30 cm focus. FIG. 14C is a speckle target image demonstrating the relative beam width for the transmit beam focused at 7 cm. These images show the same relationship between the beams as the measured beam plots (FIGS. 11-13). In FIG. 14C, the focused beam converges at 7 cm, where the brightness in the image is at its maximum value. In FIG. 14A, the unfocused beam converges, but does not reach its natural focus (i.e., the transition distance). In FIG. 14B, the negatively focused beam converges, although not as quickly as the other two.

Figure 15A:
FIG. 15A is an image of a resolution target with focused transmit.
Figure 15B:
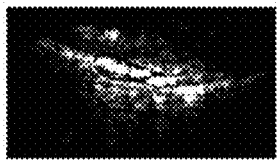
FIG. 15B is an image of the resolution target of FIG. 15A with unfocused transmit.
Figure 15C:
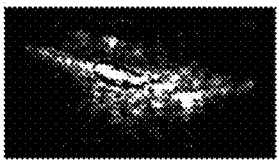
FIG. 15C is an image of the resolution target of FIG. 15A with defocused transmit.
Figure 15D:
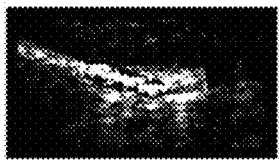
FIG. 15D is an image of the resolution target of FIG. 15A acquired at 1000 frames per second.

IMAGE QUALITY—Images of the resolution target taken with different transmit configurations can be seen in FIGS. 15A-15C. Wires in the target are spaced 1, 2, 3, and 4 mm apart, left to right in each of FIGS. 15A-15D. FIG. 15A is an image of a resolution target with focused transmit. For the focused transmit beam in FIG. 15A, all targets are clearly resolved. With this transmit configuration, the system has 1 mm or 0.8° lateral resolution. FIG. 15B is an image of the resolution target with unfocused transmit. FIG. 15C is an image of the resolution target with defocused transmit. For these transmit configurations, unfocused in FIG. 15B and defocused in FIG. 15C, the 2-mm-spaced targets are clearly resolved, whereas the 1-mm-spaced targets are not. The lateral resolution for these configurations is 2 mm, or 1.6°. FIG. 15D is an image of the resolution target acquired at 1000 frames per second. When increasing the number of image lines received per transmit to 32 to acquire at 1000 fps, the lateral resolution is unaffected, as seen in FIG. 15D. The range resolution was 1 mm in all cases.

Figure 16A:
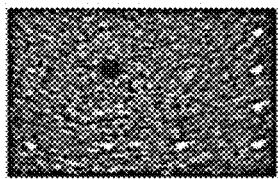
FIG. 16A is an image of a tissue-mimicking phantom acquired with focused transmit.
Figure 16B:
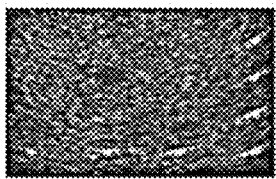
FIG. 16B is an image of the tissue-mimicking phantom of FIG. 16A acquired with unfocused transmit.
Figure 16C:
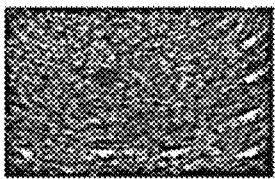
FIG. 16C is an image of the tissue-mimicking phantom of FIG. 16A acquired with defocused transmit.
Figure 16D:
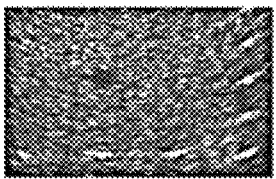
FIG. 16D is an image of the tissue-mimicking phantom of FIG. 16A acquired at 1000 frames per second.
Figure 17A:
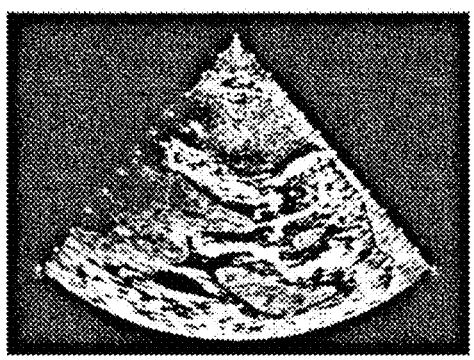
FIG. 17A is an image in the PLAX view acquired in a 59-year-old female subject during late diastole with an acquisition rate of 60 Hz.
Figure 17B:
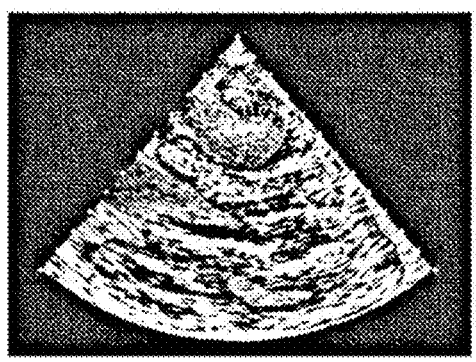
FIG. 17B is an image in the PLAX view acquired in the subject of FIG. 17A during late diastole with an acquisition rate of 240 Hz.
Figure 17C:
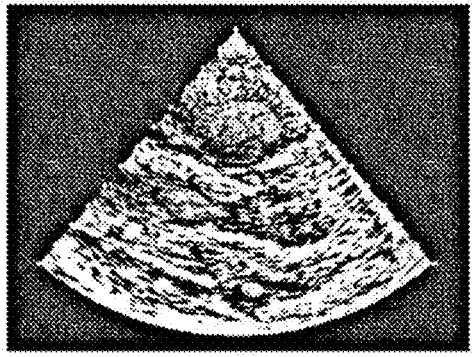
FIG. 17C is an image in the PLAX view acquired in the subject of FIG. 17A with an acquisition rate of 500 Hz.
Figure 17D:
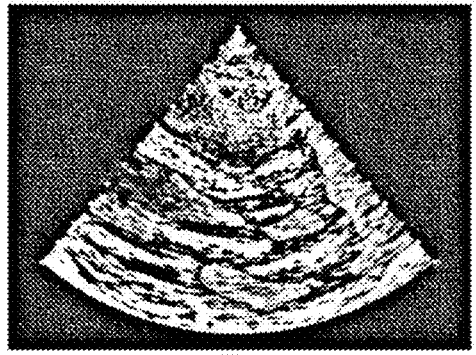
FIG. 17D is an image in the PLAX view acquired in the subject of FIG. 17A with an acquisition rate of 1000 Hz.
Figure 18A:
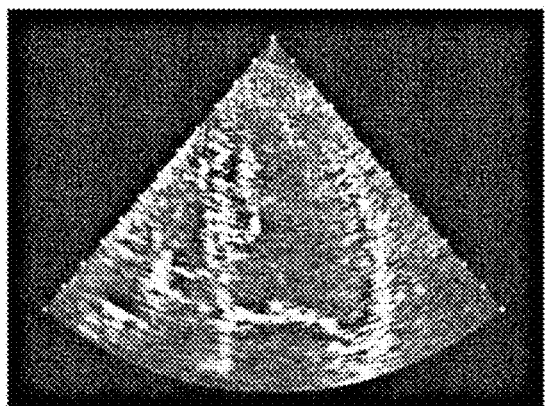
FIG. 18A is an image in the AP4 view acquired in an 81-year-old female subject during late systole with an acquisition rate of 60 Hz.
Figure 18B:
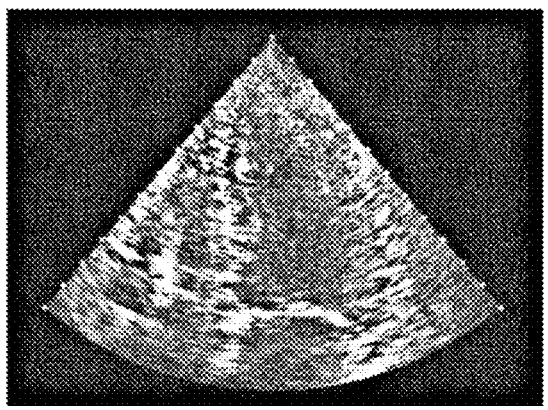
FIG. 18B is an image in the AP4 view acquired in the subject of FIG. 18A during late diastole with an acquisition rate of 240 Hz.
Figure 18C:
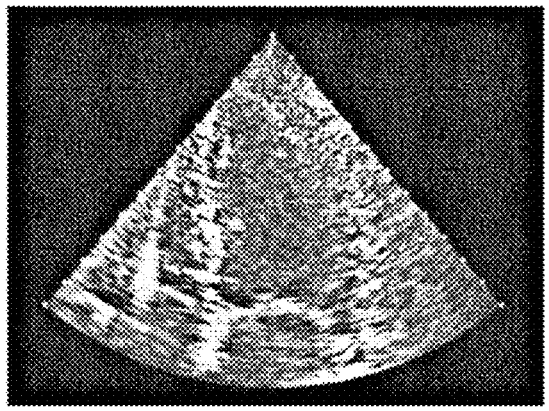
FIG. 18C is an image in the AP4 view acquired in the subject of FIG. 18A with an acquisition rate of 500 Hz.
Figure 18D:
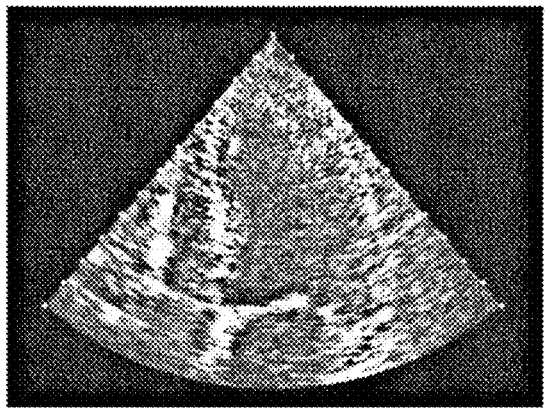
FIG. 18D is an image in the AP4 view acquired in the subject of FIG. 18A with an acquisition rate of 1000 Hz.

Images of the tissue-mimicking phantom are shown in FIGS. 16A-16D. An anechoic void used to calculate the contrast ratio can be seen in the upper left quarter of each image. The anechoic void is 0.5 cm in diameter. FIG. 16A is an image of the tissue-mimicking phantom acquired with focused transmit. FIG. 16B is an image of the tissue-mimicking phantom of FIG. 16A acquired with unfocused transmit. FIG. 16C is an image of the tissue-mimicking phantom of FIG. 16A acquired with defocused transmit. FIG. 16D is an image of the tissue-mimicking phantom of FIG. 16A acquired at 1000 frames per second. The contrast ratio was calculated to be 25.7 dB for the focused transmit (FIG. 16A), 11.5 dB for the unfocused (FIG. 16B), and 10.9 dB for the defocused transmit (FIG. 16C). When imaging at 1000 fps (FIG. 16D), the contrast ratio was 10.2 dB.

ADULT CARDIAC IMAGES—Images of adult hearts were acquired at various FRs using the transmit beams listed in Table I. Images in both the parasternal long axis (PLAX) and apical four-chamber (AP4) views can be seen in FIGS. 17A-17D and 18A-18D, respectively.

TABLE I

Transmit and Receive Schemes for In Vivo Imaging

| Frame rate (fps) | Transmit focus (cm) | Receive explosos |
|---|---|---|
| 60 | +7 | 2 |
| 240 | −30 | 8 |
| 500 | −30 | 16 |
| 1000 | −30 | 32 |

FIGS. 17A-17D are images in the PLAX view acquired in a 59-year-old female subject taken with different acquisition rates. The views in FIGS. 17A-17D were taken from late diastole when both aortic and mitral valves are distinct features in the image. Other notable features in these images are the right ventricle (RV) and the anterior wall of the RV at the apex of the image, the interventricular septum (IVS), and the left ventricle (LV). FIGS. 17A-17D were acquired with acquisition rates of 60 Hz, 240 Hz, 500 Hz and 1000 Hz, respectively.

FIGS. 18A-18D are images in the AP4 view acquired in an 81-year-old female subject during late systole with different acquisition rates. Apical views in FIGS. 18A-18D were taken from late systole so that both septal and lateral walls are within the field of view, in the center and on the right side of the image, respectively. The mitral valve separating the left atrium (LA) from the LV is closed in all images. The patient's right atrium (RA) and RV, as well as the tricuspid valve separating the two, can be seen in all images. FIGS. 18A-18D were acquired with acquisition rates of 60 Hz, 240 Hz, 500 Hz and 1000 Hz, respectively.

In both sets of images (FIGS. 17A-17B, 18A-18B), signal to noise is greater at 60 fps than at 240, 500, or 1000 fps due to the loss in signal caused by widening the transmit beam; however, there is no appreciable difference in image quality between the higher FR images.

DISCUSSION—To correlate electrical events as measured by the EKG to mechanical events seen in ultrasonic images, comparable sampling rates may be advantageous.

The AHA/ACC consensus for EKG measurements indicates a minimum sampling rate of 500 Hz. Echocardiographic images, therefore, may advantageously be acquired at a minimum of 500 per second for correlative studies between the images and EKG measurements.

High-frame-rate echocardiography was earlier described in a preliminary study. Using a high-speed video camera to capture ultrasound images displayed on a phosphorous screen, FRs up to 240 per second were achieved. At that time, the technique proved too cumbersome for clinical applications. Advances in digital memory storage and processing speeds now make possible even faster image acquisition rates, their storage, and playback at various slower speeds.

For the high FR system described herein, a beam characteristic of note is the average beam width. In this approach, the beam width used for imaging can be determined by the receive resolution of the system and the number of parallel image lines desired or available for each transmit beam. As a system according to at least one embodiment has a hardware limitation of 32 received image lines per transmit and the transducer used has a Rayleigh resolution limit of 1.2° at 3.5 MHz, an optimized beam width for this application would be 16°, assuming that the image is spatially oversampled at 0.5° intervals. Both the unfocused transmit and the defocused transmit beams satisfy this criterion; however, the unfocused transmit beam narrows significantly with range resulting in uneven signal level at deeper ranges.

For the defocused beam, the negative focus of 30 cm can be chosen for imaging because, in diffractive optics, placing a point source at the secondary focus of a diverging lens will produce an optical beam that is a projection of the aperture. This may not be the best location of the negative focus because the resulting beam has an average width of 8° wider than necessary. By combining apodization with a different negative focal length, a transmit beam that is confined to a narrower and more consistent width may be produced.

As the ripple in the main beam was found to be only 2.4 dB, this amount of variation in signal amplitude was deemed acceptable for preliminary clinical imaging due to the signal compression used in hardware processing and brightness transfer functions. Inspection of the beam images in FIGS. 14A-14B evinces no perceivable difference in brightness laterally across the beams, reflecting the negligible effect of beam ripple on the resultant images. This difference in amplitude, however, may have an effect on measurement techniques for high FR images.

An apodization scheme to minimize the ripple in the main beam may be implemented. As seen in FIGS. 15A-15D and 16A-16D, both lateral resolution and contrast are reduced when using a broadened transmit beam. The overall resolution in the images, however, is not greatly effected as long as receive resolution is maintained. The loss of 13 to 15 dB in image contrast is significant. It should be noted that the phantom used presents a case more extreme than in typical cardiac imaging applications where low-contrast regions, such as the cavity of the left ventricle, are larger than 0.5 cm in diameter. The reduction of image quality for in vivo images, specifically in lateral resolution and image contrast, can be readily appreciated by the naked eye as well in the quantitative image quality metrics presented. However, image quality of in vivo images was still deemed viable for clinical use by an experienced cardiologist. Given the anatomic considerations for adult cardiac imaging, namely an 80° field of view and 14-cm range, the FR achieved was 1000 per second. In other applications such as pediatric cardiology or peripheral vascular imaging where the field of view and range required are reduced, higher FRs are achievable with the system described herein.

Others have recently utilized high-acquisition-rate ultrasonic methods to investigate physiologic processes in the heart, most commonly the electromechanical coupling of myocardial tissue. Multiple studies have measured propagating phenomena in adult myocardial tissue that propagate at velocities of 1 to 9 m/s and occur in the time domain of the EKG that would indicate a correlation to electromechanical events. At conventional imaging rates of 60 fps, these phenomena would move 1.6 to 15 cm from frame to frame, making detection and measurement of these phenomena difficult if not impossible. However, those studies have yet to describe a real-time system with live display.

Descriptions herein demonstrate the clinical significance of temporal sampling at much higher rates than previously used in echocardiography. The systems and methods described herein allow for the extension of diagnostic ultrasound imaging to higher temporal sampling and support one of the main strengths of diagnostic ultrasound, real-time imaging. The availability of real-time, high-speed images at rates comparable to EKG sampling opens up new possibilities for studying cardiac functions in the healthy and sick. For example, high-speed images permit a more accurate determination of contractile events, such as strain, or the performance of cardiac valves. This demonstrates the ability to acquire realtime, high-speed ultrasound images in a clinical context without reducing FOV and with minimal reduction of image resolution. As these high-speed techniques are applied to the clinical situation, numerical processing techniques handle the increased data generated from each patient. The extension of these methods to real-time, high-speed 3-D imaging allow for a more complete understanding of the complicated electrical and mechanical interactions of the heart.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A method of generating an enhanced image, the method comprising:
   acquiring multiple sequential scans, in each of the scans:
      emitting, by multiple ultrasonic elements of an array, multiple respective ultrasonic signals into a subject, the multiple respective ultrasonic signals defining at least two beam portions traveling in different directions;
      receiving, by the multiple ultrasonic elements, multiple respective ultrasonic echo signals;
      generating, by the multiple ultrasonic elements, multiple respective receive signals caused by the ultrasonic echo signals; and
      storing scan data of the subject using the multiple receive signals;
   combining the scan data of two or more of the multiple sequential scans using weights to implement at least one of temporal and spatial processing; and
   generating at least one enhanced image of a portion or all of the subject using the combined scan data.

2. The method of claim 1, wherein emitting, by multiple ultrasonic elements of an array, multiple respective ultrasonic signals into the subject comprises emitting a negatively focused wavefront comprising the at least two beam portions traveling in the different directions.

3. The method of claim 2, wherein emitting, by multiple ultrasonic elements of an array, multiple respective ultrasonic signals into the subject comprises emitting a negatively focused wavefront having the at least two beam portions traveling in the different directions.

4. The method of claim 2, wherein emitting, by multiple ultrasonic elements of an array, multiple respective ultrasonic signals into the subject comprises emitting at least two negatively focused wavefronts, each comprising at least one of the at least two beam portions traveling in the different directions.

5. The method of claim 4, wherein emitting at least two negatively focused wavefronts comprises:
sending a first negatively focused wavefront from a first subgroup of multiple ultrasonic elements of the array; and
sending a second negatively focused wavefront from a second subgroup of multiple ultrasonic elements of the array.

6. The method of claim 4, wherein:
the array defines an array aperture in which the multiple ultrasonic elements of the array are positioned;
the first subgroup defines a first sub-aperture in which the multiple ultrasonic elements of the first subgroup are positioned;
the second subgroup defines a second sub-aperture in which the multiple ultrasonic elements of the second subgroup are positioned; and
the first sub-aperture and second sub-aperture as smaller than the array aperture.

7. The method of claim 6, wherein the first and second sub-apertures overlap.

8. The method of claim 1, wherein generating at least one enhanced image comprises generating displayed images in real time.

9. The method of claim 1, further comprising saving data comprising information about the multiple respective ultrasonic echo signals, and wherein generating at least one enhanced image comprises generating displayed images using the saved data.

10. The method of claim 9, wherein generating at least one enhanced image comprises generating a series of selectable view-rate displayed images using the saved data.

11. The method of claim 1, further comprising subtracting stored data to show blood flow.

12. The method of claim 1, wherein the multiple sequential scans are acquired at rates of at least 150 scans per second.

13. The method of claim 1, wherein combining the scan data of two or more of the multiple sequential scans using weights to implement at least one of temporal and spatial processing comprises calculating an absolute difference in brightness between each pixel of at least two of the scans.

14. The method of claim 13, wherein generating at least one enhanced image of a portion or all of the subject using the combined scan data comprises generating each pixel of the enhanced image based on the calculated absolute difference in brightness between each pixel of at least two of the scans.

15. The method of claim 1, wherein the multiple sequential scans are acquired at rates of at least 500 scans per second.

* * * * *